(12) United States Patent
Breuil et al.

(10) Patent No.: US 10,300,473 B2
(45) Date of Patent: May 28, 2019

(54) CATALYTIC COMPOSITION COMPRISING NICKEL AND A LIGAND OF THE PHOSPHANE COMPLEXED WITH NICKEL TYPE, AND USE THEREOF IN A OLEFIN OLIGOMERISATION METHOD

(71) Applicant: IFP Energies nouvelles, Rueil-Malmaison (FR)

(72) Inventors: Pierre-Alain Breuil, Lyons (FR); Olivia Chaumet-Martin, Brignais (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/748,494

(22) PCT Filed: Apr. 20, 2016

(86) PCT No.: PCT/EP2016/058807
§ 371 (c)(1),
(2) Date: Jan. 29, 2018

(87) PCT Pub. No.: WO2017/016688
PCT Pub. Date: Feb. 2, 2017

(65) Prior Publication Data
US 2018/0221861 A1  Aug. 9, 2018

(30) Foreign Application Priority Data

Jul. 29, 2015 (FR) .................................. 15 57248

(51) Int. Cl.
| | | |
|---|---|---|
| *C07C 2/36* | (2006.01) | |
| *C07C 29/16* | (2006.01) | |
| *C07C 45/50* | (2006.01) | |
| *B01J 31/24* | (2006.01) | |
| *B01J 31/14* | (2006.01) | |

(52) U.S. Cl.
CPC ......... *B01J 31/2414* (2013.01); *B01J 31/143* (2013.01); *B01J 31/24* (2013.01); *B01J 31/2404* (2013.01); *C07C 2/36* (2013.01); *C07C 29/16* (2013.01); *C07C 45/50* (2013.01); *B01J 2231/20* (2013.01); *B01J 2531/847* (2013.01); *C07C 2531/14* (2013.01); *C07C 2531/24* (2013.01)

(58) Field of Classification Search
CPC .......... C07C 2/36; C07C 29/16; C07C 45/50; B01L 31/2414; B01L 31/24
See application file for complete search history.

(56) References Cited

U.S. PATENT DOCUMENTS

| | | |
|---|---|---|
| 3,485,881 A | 12/1969 | Zuech |
| 3,485,892 A | 12/1969 | Griffin, Jr. |
| 3,513,218 A * | 5/1970 | Meyer ....................... C07C 2/30 502/117 |

FOREIGN PATENT DOCUMENTS

GB  1211738 A  11/1970

OTHER PUBLICATIONS

International Search Report PCT/EP2016/058807 dated Jun. 24, 2016.

* cited by examiner

*Primary Examiner* — Sikarl A Witherspoon
(74) *Attorney, Agent, or Firm* — Millen White Zelano & Branigan

(57) ABSTRACT

The invention concerns a catalytic composition comprising: at least one nickel precursor with an oxidation number of (+II) containing a phosphine ligand complexed with nickel, at least one Lewis base, and at least one activating agent selected from the group formed by chlorinated and brominated hydrocarbylaluminium compounds, used alone or as a mixture, in a manner such that the molar ratio of the ensemble of the Lewis base and phosphine ligand complexed with the nickel of the composition to the nickel is in the range 5 to 30. The invention also concerns the use of said catalytic composition.

17 Claims, No Drawings

CATALYTIC COMPOSITION COMPRISING NICKEL AND A LIGAND OF THE PHOSPHANE COMPLEXED WITH NICKEL TYPE, AND USE THEREOF IN A OLEFIN OLIGOMERISATION METHOD

The present invention relates to a novel composition based on nickel and to its use as a catalyst in chemical transformation reactions, and in particular in a process for the oligomerization of an olefinic feed.

The invention also relates to a process for the oligomerization of an olefin feed, comprising bringing said feed into contact with the nickel-based composition in accordance with the invention, and in particular to a process for the dimerization of ethylene to 1-butene in particular, using said nickel-based composition in accordance with the invention.

PRIOR ART

The transformation of ethylene using a homogeneous nickel catalyst has been studied since 1950. That research has resulted in the development and commercialization of various processes.

The development of catalytic systems which are capable of dimerizing ethylene into butenes is based on the choice of metal and of suitable ligands. In among the existing systems, a number of catalytic systems based on nickel using phosphine-type ligands have been developed.

Thus, the U.S. Pat. No. 5,237,118 B describes a process for the oligomerization of ethylene employing a catalytic composition comprising a nickel compound with an oxidation number of zero, and a phosphine ligand in proportions which vary with respect to the nickel compound. That patent also describes the use of an organic fluorinated acid for carrying out the oligomerization process.

U.S. Pat. No. 4,242,531 B describes a process for the dimerization of olefins and employs a catalytic system based on chlorinated nickel compounds with an oxidation number of +2 and an activator of the halogenated alkylaluminium type. That patent envisages the production of 2-butene compounds.

Patent FR 1 547 921 describes a catalytic composition based on nickel halide and phosphine which requires a prior reduction of the composition with a view to the preparation of the active catalyst. The butenes yields are of the order of 63% C4, 3% of which is 1-butene.

Patent FR 1 588 162 describes a process for the dimerization of C2 to C4 olefins employing a catalytic system comprising a nickel compound and a phosphine, and in particular alkyl halides with butenes yields of the order of 80%. That patent envisages the production of 2-butenes.

Thus, there is still a need for the development of novel catalytic compositions which perform better in terms of yield and selectivity for the oligomerization of olefins, in particular for the dimerization of ethylene, in particular to form 1-butene.

The Applicant's research has resulted in the development of a novel catalytic composition comprising at least one nickel precursor, preferably halogenated, with an oxidation number of (+II) and containing a phosphine ligand complexed with nickel, at least one Lewis base, and at least one activating agent selected from the group formed by chlorinated or brominated hydrocarbylaluminium compounds, used alone or as a mixture, in a manner such that the molar ratio of the ensemble of the Lewis base and phosphine ligand complexed with nickel of the composition to the nickel is in the range 5 to 30. It has surprisingly been shown that compositions of this type have interesting catalytic properties. In particular, these compositions have a good yield/catalytic selectivity in the oligomerization of olefins, more precisely in the dimerization of ethylene to 1-butene.

One aim of the invention is to provide a novel composition based on nickel. Another aim of the invention is to propose a novel catalytic system comprising said composition for chemical transformation reactions, in particular for the oligomerization of olefins, especially for the dimerization of ethylene to form 1-butene.

DETAILED DESCRIPTION OF THE INVENTION

Composition in Accordance with the Invention

The catalytic composition in accordance with the invention comprises:
  at least one nickel precursor with an oxidation number of (+II) containing a phosphine ligand complexed with nickel,
  at least one Lewis base,
  and at least one activating agent selected from the group formed by chlorinated and brominated hydrocarbylaluminium compounds, used alone or as a mixture,
in a manner such that the molar ratio of the ensemble of the Lewis base and phosphine ligand provided by the nickel precursor to the nickel provided by said precursor is in the range 5 to 30.

The nickel precursor in accordance with the invention is advantageously represented by the following formula: $NiX_2(PR^1R^2R^3)_2$, in which the groups $R^1$, $R^2$ and $R^3$, which may be identical or different, and which may or may not be bonded together, are selected from aromatic groups which may or may not be substituted and which may or may not contain heteroelements and/or from hydrocarbyl groups which may or may not be cyclic, which may or may not be substituted and which may or may not contain heteroelements, and in which X is selected from halogens such as chlorine, bromine or iodine or aromatic groups which may or may not be substituted and which may or may not contain heteroelements, and/or from hydrocarbyl groups which may or may not be cyclic, which may or may not be substituted and which may or may not contain heteroelements; preferably, X is chlorine or bromine.

The aromatic groups $R^1$, $R^2$ and $R^3$ of the phosphine ligand $PR^1R^2R^3$ complexed with nickel are preferably selected from the group formed by phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bis-naphthyl, pyridyl, bisphenyl, furanyl and thiophenyl groups.

The hydrocarbyl groups $R^1$, $R^2$ and $R^3$ of the phosphine ligand $PR^1R^2R^3$ complexed with nickel advantageously contain 1 to 20 carbon atoms, preferably 2 to 15 carbon atoms, more preferably between 3 and 10 carbon atoms. Preferably, the $R^1$, $R^2$ and $R^3$ hydrocarbyl groups of the phosphine ligand $PR^1R^2R^3$ complexed with nickel are selected from the group formed by the groups methyl, ethyl, propyl, isopropyl, n-butyl, tert-butyl, pentyl, cyclopentyl, hexyl, cyclohexyl, octyl, 2-ethylhexyl, benzyl and adamantyl.

Preferred nickel precursors are selected from bis(trimethylphosphine) nickel dichloride, bis(triethylphosphine) nickel dichloride, bis(triisopropylphosphine) nickel dichloride, bis(tri-n-butylphosphine) nickel dichloride, bis(tri-isobutylphosphine) nickel dichloride, bis(tri-tert-butylphosphine) nickel dichloride, bis(tripentylphosphine) nickel dichloride, bis(tricyclopentylphosphine) nickel dichloride, bis(trihexylphosphine) nickel dichloride, bis(tricyclohexylphosphine) nickel dichloride, bis(tri(2-ethylhexyl)phosphine) nickel dichloride, bis(trioctylphosphine) nickel dichloride, bis(triphenylphosphine) nickel dichloride, bis(tri(2-tolyl)phosphine) nickel dichloride, bis(tri(3-tolyl)phosphine) nickel dichloride, bis(tri(4-tolyl)phosphine) nickel dichloride, bis(tri(2-naphthyl)phosphine) nickel dichloride, bis(tribenzylphosphine) nickel dichloride, used alone or as a mixture.

The nickel precursors described in the invention are prepared using techniques which are known to the person skilled in the art, such as those described in the publication *Organometallics*, 2014, 33, 2012-2018 or the patent U.S. Pat. No. 4,176,086.

The catalytic composition in accordance with the invention also comprises a Lewis base. Within the context of the present invention, the term "Lewis base" should be understood to mean any chemical entity wherein one constituent has one or more pairs of electrons which are free or non-bonding. The Lewis bases in accordance with the invention in particular correspond to any entity comprising an oxygen atom, a phosphorus atom or a nitrogen atom having a pair of free or non-bonding electrons, or a π double bond which is capable of forming a $\eta^2$ type bond with the nickel, in particular any entity comprising an oxygen atom, a phosphorus atom or a nitrogen atom having a pair of free electrons or non-bonding electrons.

The Lewis base of the invention is preferably selected from diethyl ether, methyl tert-butyl ether, tetrahydrofuran, 1,4-dioxane, isoxazole, pyridine, pyrazine, pyrimidine, and phosphines with formula $PR^{'1}R^{'2}R^{'3}$ in which the groups $R^{'1}$, $R^{'2}$ and $R^{'3}$, which are identical, which may or may not be bonded together, are selected from aromatic groups which may or may not be substituted and which may or may not contain heteroelements and/or from aromatic groups which may or may not be substituted and which may or may not contain heteroelements, and preferably from phosphines with formula $PR^{'1}R^{'2}R^{'3}$, $R^{'1}$, with $R^{'2}$ and $R^{'3}$ having the definition given above, pyridine, 1,4-dioxane and tetrahydrofuran.

The aromatic groups $R^{'1}$, $R^{'2}$ and $R^{'3}$ of the phosphine $PR^{'1}R^{'2}R^{'3}$ are preferably selected from the group formed by phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl and thiophenyl groups.

The hydrocarbyl groups $R^{'1}$, $R^{'2}$ and $R^{'3}$ of the phosphine $PR^{'1}R^{'2}R^{'3}$ advantageously contain 1 to 20 carbon atoms, preferably 2 to 15 carbon atoms, more preferably in the range 3 to 10 carbon atoms. Preferably, the hydrocarbyl groups $R^{'1}$, $R^{'2}$ and $R^{'3}$ of the phosphine $PR^{'1}R^{'2}R^{'3}$ are selected from the group formed by methyl, ethyl, propyl, isopropyl, n-butyl, tert-butyl, pentyl, cyclopentyl, hexyl, cyclohexyl, octyl, 2-ethylhexyl, benzyl and adamantyl groups.

In accordance with the invention, the molar ratio of the ensemble of the Lewis base and the phosphine ligand provided by the nickel precursor to the nickel provided by said precursor is in the range 5 to 25, preferably in the range 5 to 20, more preferably in the range 5 to 15. Preferably, this molar ratio is in the range 6 to 30, preferably in the range 6 to 25, more preferably in the range 6 to 20, and still more preferably in the range 6 to 15.

For greater clarity, it should be understood in the context of the present invention that the expression of this molar ratio means that the number of moles of phosphine ligands present in the nickel precursor is taken into account in the calculation of the molar ratio; in addition, the number of moles of phosphine ligands provided in the nickel precursor is supplemented by the number of moles of Lewis base in the composition then made with reference to the number of moles of nickel provided by the nickel precursor.

Advantageously, in accordance with the invention, the molar ratio of the activating agent to the ensemble of the Lewis base and phosphine provided by the nickel precursor of the composition is 1 or more, preferably 1.5 or more, more preferably 2 or more.

In accordance with the invention, the activating agent employed in the catalytic composition in accordance with the invention is preferably selected from the group formed by chlorinated and brominated hydrocarbylaluminium compounds, used alone or as a mixture.

Advantageously, said activating agent is selected from the group formed by methylaluminium dichloride ($MeAlCl_2$), ethylaluminium dichloride ($EtAlCl_2$), ethylaluminium sesquichloride ($Et_3Al_2Cl_3$), diethylaluminium chloride ($Et_2AlCl$), diisobutylaluminium chloride ($iBu_2AlCl$) and isobutylaluminium dichloride ($iBuAlCl_2$), used alone or as a mixture.

In accordance with the invention, the molar ratio of the activating agent to the nickel precursor is preferably 5 or more, more preferably 6 or more, and preferably 30 or less, preferably 25 or less, more preferably 20 or less.

The molar ratios cited in the present invention, in particular with respect to the nickel precursor, should be understood to be expressed with respect to the number of moles of nickel provided to the catalytic composition.

The compositions in accordance with the invention may also optionally comprise a solvent. A solvent may be used which is selected from organic solvents and in particular from ethers, alcohols, chlorinated solvents and saturated, unsaturated, aromatic or non-aromatic, cyclic or non-cyclic hydrocarbons. Preferably, the solvent is selected from hexane, cyclohexane, methylcyclohexane, heptane, butane or isobutane or any other hydrocarbon cut with boiling points of more than 70° C., preferably in the range 70° C. to 200° C. and preferably in the range 90° C. to 180° C., monoolefins or diolefins preferably containing 4 to 20 carbon atoms, cycloocta-1,5-diene, benzene, toluene, orthoxylene, mesitylene, ethylbenzene, dichloromethane, chlorobenzene, methanol, ethanol, pure or as a mixture, and ionic liquids. In the case in which the solvent is an ionic liquid, it is advantageously selected from the ionic liquids described in patents U.S. Pat. No. 6,951,831 B2 and FR 2 895 406 B1.

Use of the Composition in Accordance with the Invention

The compositions in accordance with the invention may be used as a catalyst in a chemical transformation reaction such as hydrogenation, hydroformylation, cross-coupling or olefin oligomerization reactions. In particular, these compositions are used in a process for the oligomerization of a feed of olefins advantageously containing 2 to 10 carbon atoms.

Preferably, the oligomerization process is a process for the dimerization of ethylene, in particular to form 1-butene.

The oligomerization process of the invention is advantageously operated in the presence of a solvent.

The solvent of the oligomerization process may be selected from organic solvents, and preferably from chlorinated solvents and saturated, unsaturated, aromatic or non-aromatic, cyclic or non-cyclic hydrocarbons. In particular, said solvent is selected from hexane, cyclohexane, methylcyclohexane, heptane, butane or isobutane, mono-olefins or diolefins preferably containing 4 to 20 carbon atoms, benzene, toluene, ortho-xylene, mesitylene, ethylbenzene, dichloromethane, chlorobenzene, pure or as a mixture, and ionic liquids. In the case in which said reaction solvent is an ionic liquid, it is advantageously selected from the ionic liquids described in patents U.S. Pat. No. 6,951,831 B2 and FR 2 895 406 B1.

Oligomerization is defined as the transformation of a monomeric unit into a compound or mixture of compounds with general formula $C_pH_{2p}$, wherein $4 \leq p \leq 80$, preferably wherein $4 \leq p \leq 50$, more preferably wherein $4 \leq p \leq 26$ and still more preferably wherein $4 \leq p \leq 14$.

The olefins used in the oligomerization process are olefins containing 2 to 10 carbon atoms. Preferably, said olefins are selected from ethylene, propylene, n-butenes and n-pentenes, alone or as a mixture, pure or diluted.

In the case in which said olefins are diluted, said olefins are diluted with one or more alkane(s) or any other oil cut such as those found in "cuts" obtained from oil refining processes or from petrochemicals, such as from catalytic cracking or steam cracking.

Preferably, the olefin used in the oligomerization process is ethylene.

Said olefins may originate from non-fossil sources such as biomass. As an example, the olefins used in the oligomerization process in accordance with the invention may be produced from alcohols, and in particular by dehydration of alcohols.

The concentration of nickel in the catalytic solution is advantageously in the range $1 \times 10^{-8}$ to $1$ mol/L, preferably in the range $1 \times 10^{-6}$ to $1 \times 10^{-2}$ mol/L.

The oligomerization process is advantageously operated at a total pressure in the range from atmospheric pressure to 20 MPa, preferably in the range 0.1 to 8 MPa, and at a temperature in the range $-40°$ C. to $+250°$ C., preferably in the range $-20°$ C. to $150°$ C.

The heat caused by the reaction may be eliminated using any of the means known to the person skilled in the art.

The oligomerization process may be carried out in a closed system, in a semi-open system or continuously, with one or more reaction steps. Vigorous stirring is advantageously carried out in order to ensure good contact between the reagent or reagents and the catalytic system.

The oligomerization process may be carried out batchwise. In this case, a selected volume of the solution comprising the composition in accordance with the invention is introduced into a reactor, preferably provided with the usual stirring, heating and cooling devices.

The oligomerization process may also be carried out continuously. In this case, the solution comprising the composition in accordance with the invention is injected into a reactor in which the olefin is reacted, preferably with the temperature being controlled.

The catalytic composition is destroyed using any usual means known to the person skilled in the art, then the reaction products as well as the solvent are separated, for example by distillation. The olefin which has not been transformed may be recycled to the reactor.

The process of the invention may be carried out in a reactor having one or more reaction stages in series, the olefinic feed and/or the catalytic composition having already been pre-conditioned and introduced continuously, either into the first stage, or into the first and any of the other stages. At the outlet from the reactor, the catalytic composition may be deactivated, for example by injecting an amine which may or may not be diluted and/or an aqueous basic solution and/or an aqueous acidic solution. The unconverted olefins and any alkanes present in the feed are then separated from the oligomers by distillation.

The products of the present process may be of application, for example as components of fuels for automobiles, as feeds in a hydroformylation reaction for the synthesis of aldehydes and alcohols, as components for the chemical, petrochemical, pharmaceutical or perfumery industry and/or as feeds in a metathesis process for the synthesis of propylene and/or as a feed for a process for the production of butadiene via an oxidizing dehydrogenation or via a step for metallic catalysis, for example.

The following examples illustrate the invention without limiting its scope.

EXAMPLES

Implementation of Catalytic Test:

The reactor had previously been dried under vacuum and placed under an atmosphere of ethylene. 93 mL of n-heptane was introduced into the reactor under an atmosphere of ethylene. 6 mL of a solution containing the nickel complex bis(tri-n-butylphosphine) nickel dichloride $NiCl_2(P(nBu)_3)_2$ or bis(tricyclohexylphosphine) nickel dichloride $NiCl_2(PCy_3)_2$ (5 or 10 μmol) and optionally the phosphine tri-n-butylphosphine or $P(nBu)_3$ or tricyclohexylphosphine or $PCy_3$, pyridine or tetrahydrofuran (40, 80 or 130 μmol) were then introduced into the reactor. Between 1 and 2 g of ethylene was then dissolved in the reactor, stirring was commenced and the temperature was programmed to $40°$ C. After degassing the reactor, the temperature was programmed to $45°$ C. (test temperature). 1 mL of a solution of ethylaluminium dichloride (75 or 150 μmol) was then introduced. The reactor was pressurized to the test pressure (20 bar). The ethylene consumption was monitored until 50 g of ethylene had been introduced. The supply of ethylene was then cut off. The gas phase was quantified and qualified by GC, the liquid phase was weighed, neutralized and qualified by GC.

Catalytic Tests

Examples 1-3: Study of Nickel Precursor $NiCl_2(P(nBu)_3)_2$

| Example | Catalytic precursor | Lewis base (eq) | Time (min) | Mass of $C_2H_4$ cons. (g) | % C4** | % C6 | % C8+ | % 1-C4*** |
|---|---|---|---|---|---|---|---|---|
| 1* | $NiCl_2(P(nBu)_3)_2$ | — | 7 | 50 | 92 | 8 | 0 | 5 |
| 2 | $NiCl_2(P(nBu)_3)_2$ | $P(nBu)_3$ (8) | 20 | 13 | 98 | 2 | 0 | 51 |
| 3 | $NiCl_2(P(nBu)_3)_2$ | $PCy_3$ (8) | 30 | 21 | 98 | 2 | 0 | 66 |

$n_{Ni}$ = 5 μmol, 15 eq. $EtAlCl_2$, $45°$ C., 2 MPa, 100 mL n-heptane.
*Comparative example. cons. = consumed. eq = molar equivalent,
**yield of C4 corresponds to percentage by weight of the C4 cut formed in the products,
***percentage of 1-C4 in the C4 cut.

Examples 4-10: Study of Nickel Precursor $NiCl_2(PCy_3)_2$

| Example | catalytic precursor | Lewis base (eq) | time (min) | Mass of $C_2H_4$ cons. (g) | % C4** | % C6 | % C8+ | % 1-C4*** |
|---|---|---|---|---|---|---|---|---|
| 4* | $NiCl_2(PCy_3)_2$ | — | 6 | 45 | 85 | 13 | 2 | 40 |
| 5 | $NiCl_2(PCy_3)_2$ | $PCy_3$ (8) | 13 | 37 | 92 | 7 | 1 | 90 |
| 6$^a$ | $NiCl_2(PCy_3)_2$ | $PCy_3$ (13) | 23 | 35 | 95 | 5 | 0 | 95 |
| 7$^a$ | $NiCl_2(PCy_3)_2$ | Pyridine (8) | 8 | 43 | 89 | 10 | 1 | 71 |
| 8$^a$ | $NiCl_2(PCy_3)_2$ | Pyridine (13) | 7 | 12 | 96 | 4 | 0 | 97 |
| 9$^a$ | $NiCl_2(PCy_3)_2$ | THF (8) | 7 | 18 | 90 | 9 | 1 | 76 |
| 10$^a$ | $NiCl_2(PCy_3)_2$ | THF (13) | 10 | 11 | 96 | 4 | 0 | 96 |

$n_{Ni}$ = 5 µmol, 15 eq. $EtAlCl_2$, 45° C., 2 MPa, 100 mL n-heptane.
*Comparative example.
$^a n_{Ni}$ = 10 µmol. cons. = consumed. eq = molar equivalent,
**yield of C4 corresponds to percentage by weight of the C4 cut formed in the products,
***percentage of 1-C4 in the C4 cut.

It can be seen that the catalytic compositions in accordance with the invention (Examples 2, 3, 5, 6, 7, 8, 9 and 10) can be used to obtain a butenes cut (C4) in a yield of at least 89% and a selectivity for 1-butene (1-C4) of at least 51% compared with catalytic compositions not in accordance with the invention (Examples 1 and 4) which had a maximum yield of 92% of C4 and a selectivity for 1-butene (1-C4) in the range 5% to 40%.

The invention claimed is:

1. A catalytic composition comprising:
   at least one nickel precursor with an oxidation number of (+II) containing a phosphine ligand complexed with nickel,
   at least one Lewis base that is diethyl ether, methyl tert-butyl ether, tetrahydrofuran, 1,4-dioxane, isoxazole, pyridine, pyrazine, or pyrimidine,
   and at least one activating agent selected from the group formed by chlorinated and brominated hydrocarbylaluminium compounds, used alone or as a mixture,
   in a manner such that the molar ratio of the ensemble of the Lewis base and phosphine ligand provided by the nickel precursor to the nickel provided by said precursor is in the range 6 to 30.

2. The composition according to claim 1, in which the molar ratio of the activating agent to the ensemble of the Lewis base and phosphine ligand provided by said nickel precursor is 1 or more.

3. The composition according to claim 1, in which the nickel precursor is represented by the formula:

$NiX_2(PR^1R^2R^3)_2$, in which the groups $R^1$, $R^2$ and $R^3$, which may be identical or different, and which may or may not be bonded together, are selected from aromatic groups which may or may not be substituted and which may or may not contain heteroelements and/or from hydrocarbyl groups which may or may not be cyclic, which may or may not be substituted and which may or may not contain heteroelements, and in which X is selected from halogens such as chlorine, bromine or iodine or aromatic groups which may or may not be substituted and which may or may not contain heteroelements, and/or from hydrocarbyl groups which may or may not be cyclic, which may or may not be substituted and which may or may not contain heteroelements.

4. The composition according to claim 1, in which the nickel precursor is selected from bis(trimethylphosphine) nickel dichloride, bis(triethylphosphine) nickel dichloride, bis(triisopropylphosphine) nickel dichloride, bis(tri-n-butylphosphine) nickel dichloride, bis(triisobutylphosphine) nickel dichloride, bis(tri-tert-butylphosphine) nickel dichloride, bis(tripentylphosphine) nickel dichloride, bis(tricyclopentylphosphine) nickel dichloride, bis(trihexylphosphine) nickel dichloride, bis(tricyclohexylphosphine) nickel dichloride, bis(tri(2-ethylhexyl)phosphine) nickel dichloride, bis(trioctylphosphine) nickel dichloride, bis(triphenylphosphine) nickel dichloride, bis(tri(2-tolyl)phosphine) nickel dichloride, bis(tri(3-tolyl)phosphine) nickel dichloride, bis(tri(4-tolyl)phosphine) nickel dichloride, bis(tri(2-naphthyl)phosphine) nickel dichloride, and bis(tribenzylphosphine) nickel dichloride, used alone or as a mixture.

5. The composition according to claim 1, in which the molar ratio of the ensemble of the Lewis base and the phosphine ligand provided by the nickel precursor to the nickel provided by said precursor is in the range 6 to 25.

6. The composition according to claim 1, in which the Lewis base is diethyl ether, methyl tert-butyl ether, tetrahydrofuran, 1,4-dioxane, isoxazole, pyridine, or pyrimidine.

7. The composition according to claim 1, in which the activating agent is selected from the group formed by chlorinated or brominated hydrocarbylaluminium compounds, used alone or as a mixture.

8. The composition according to claim 7, in which the activating agent is selected from the group formed by methylaluminium dichloride ($MeAlCl_2$), ethylaluminium dichloride ($EtAlCl_2$), ethylaluminium sesquichloride ($Et_3Al_2Cl_3$), diethylaluminium chloride ($Et_2AlCl$), diisobutylaluminium chloride ($iBu_2AlCl$) and isobutylaluminium dichloride ($iBuAlCl_2$), used alone or as a mixture.

9. A process for the oligomerization of a feed of olefins, comprising bringing said feed into contact with a composition in accordance with claim 1, wherein the reaction is an ethylene dimerization reaction.

10. The process according to claim 9, in which the feed comprises olefins containing in the range of 2 to 10 carbon atoms.

11. The process according to claim 9, carried out in a closed system, a semi-open system, a continuous or a batch system.

12. A hydroformylation process for the synthesis of aldehydes and alcohols, comprising oligomerizing olefins in the presence of a catalyst according to claim 1 to produce oligomers, and hydroformylating said oligomers to produce aldehydes and/or alcohols.

13. A metathesis process for the synthesis of propylene comprising oligomerizing olefins in the presence of a catalyst according to claim 1 to produce oligomers and subjecting said oligomers to metathesis to produce propylene.

14. A process for the production of butadiene comprising oligomerizing olefins in the presence of a catalyst according to claim 1 to produce oligomers, and subjecting said oligomers to oxidizing dehydrogenation or metallic catalysis to produce butadiene.

15. A composition according to claim 5, wherein the molar ratio of the ensemble of the Lewis base and the phosphine ligand provided by the nickel precursor to the nickel provided by said precursor is in the range of 6 to 20.

16. A composition according to claim 15, wherein the molar ratio of the ensemble of the Lewis base and the phosphine ligand provided by the nickel precursor to the nickel provided by said precursor is in the range of 6 to 15.

17. The composition according to claim 6, in which the Lewis base is tetrahydrofuran or pyridine.

* * * * *